(12) United States Patent
Aviles

(10) Patent No.: US 8,679,066 B2
(45) Date of Patent: Mar. 25, 2014

(54) STABILIZATION DEVICE WITH INTEGRATED DRESSING

(75) Inventor: Alejandro A. Aviles, Atlanta, GA (US)

(73) Assignee: C.R. Bard, Inc., Covington, GA (US)

( * ) Notice: Subject to any disclaimer, the term of this patent is extended or adjusted under 35 U.S.C. 154(b) by 39 days.

(21) Appl. No.: 13/320,405

(22) PCT Filed: May 14, 2010

(86) PCT No.: PCT/US2010/035011
§ 371 (c)(1),
(2), (4) Date: Feb. 2, 2012

(87) PCT Pub. No.: WO2010/132843
PCT Pub. Date: Nov. 18, 2010

(65) Prior Publication Data
US 2012/0123343 A1    May 17, 2012

Related U.S. Application Data

(60) Provisional application No. 61/178,928, filed on May 15, 2009.

(51) Int. Cl.
*A61M 5/32*        (2006.01)

(52) U.S. Cl.
USPC .......................................... 604/174; 604/180

(58) Field of Classification Search
USPC .................................................. 604/174–180
See application file for complete search history.

(56) References Cited

U.S. PATENT DOCUMENTS

| | | |
|---|---|---|
| 3,046,984 A | 7/1962 | Eby |
| 3,167,072 A | 1/1965 | Stone et al. |
| 3,194,235 A | 7/1965 | Cooke |
| 3,288,137 A | 11/1966 | Lund |
| 3,630,195 A | 12/1971 | Santomieri |
| 3,782,383 A | 1/1974 | Thompson et al. |
| 3,826,254 A | 7/1974 | Mellor |

(Continued)

FOREIGN PATENT DOCUMENTS

| | | |
|---|---|---|
| CA | 1 311 977 | 12/1992 |
| CA | 1 318 824 | 6/1993 |

(Continued)

OTHER PUBLICATIONS

International Search Report and Written Opinion issued on Jul. 16, 2010 for International Application No. PCT/US2010/035011.

*Primary Examiner* — Theodore Stigell
(74) *Attorney, Agent, or Firm* — Knobbe Martens Olson & Bear LLP

(57) ABSTRACT

A stabilization device for securing a medical article near an insertion site includes an anchor pad having an integral dressing portion, such as a transparent dressing portion, to allow for covering and protection of the insertion site.

20 Claims, 6 Drawing Sheets

(56) References Cited

U.S. PATENT DOCUMENTS

| | | |
|---|---|---|
| 3,900,026 A | 8/1975 | Wagner |
| 3,901,226 A | 8/1975 | Scardenzan |
| 4,082,094 A | 4/1978 | Dailey |
| 4,129,128 A | 12/1978 | McFarlane |
| D252,822 S | 9/1979 | McFarlane |
| 4,193,174 A | 3/1980 | Stephens |
| 4,224,937 A | 9/1980 | Gordon |
| 4,250,880 A | 2/1981 | Gordon |
| 4,333,468 A | 6/1982 | Geist |
| 4,470,410 A | 9/1984 | Elliott |
| 4,484,913 A | 11/1984 | Swauger |
| 4,516,968 A | 5/1985 | Marshall et al. |
| 4,517,971 A | 5/1985 | Sorbonne |
| 4,563,177 A | 1/1986 | Kamen |
| 4,632,670 A | 12/1986 | Mueller |
| 4,633,863 A | 1/1987 | Filips et al. |
| 4,645,492 A | 2/1987 | Weeks |
| 4,669,458 A * | 6/1987 | Abraham et al. ............ 128/846 |
| 4,711,636 A | 12/1987 | Bierman |
| 4,737,143 A | 4/1988 | Russell |
| 4,846,807 A | 7/1989 | Safadago |
| 4,852,844 A | 8/1989 | Villaveces |
| 4,863,432 A | 9/1989 | Kvalo |
| 4,898,587 A | 2/1990 | Mera |
| 4,976,698 A | 12/1990 | Stokley |
| 4,981,475 A | 1/1991 | Haindl |
| 4,997,421 A | 3/1991 | Palsrok et al. |
| 5,037,397 A | 8/1991 | Kalt et al. |
| 5,074,847 A | 12/1991 | Greenwell et al. |
| 5,084,026 A | 1/1992 | Shapiro |
| 5,112,313 A | 5/1992 | Sallee |
| 5,116,324 A | 5/1992 | Brierley et al. |
| 5,137,519 A | 8/1992 | Littrell et al. |
| 5,167,630 A | 12/1992 | Paul |
| 5,192,273 A | 3/1993 | Bierman |
| 5,192,274 A | 3/1993 | Bierman |
| 5,215,532 A | 6/1993 | Atkinson |
| 5,238,010 A | 8/1993 | Grabenkort |
| 5,290,248 A | 3/1994 | Bierman et al. |
| D347,060 S | 5/1994 | Bierman |
| 5,314,411 A | 5/1994 | Bierman et al. |
| 5,328,487 A | 7/1994 | Starchevich |
| 5,354,282 A | 10/1994 | Bierman |
| 5,356,391 A | 10/1994 | Stewart |
| 5,370,627 A | 12/1994 | Conway |
| 5,395,344 A | 3/1995 | Beisang et al. |
| 5,413,120 A | 5/1995 | Grant |
| 5,413,562 A | 5/1995 | Swauger |
| D359,120 S | 6/1995 | Sallee et al. |
| 5,456,671 A | 10/1995 | Bierman |
| D364,922 S | 12/1995 | Bierman |
| D375,355 S | 11/1996 | Bierman |
| D375,356 S | 11/1996 | Bierman |
| 5,577,516 A | 11/1996 | Schaeffer |
| 5,578,013 A | 11/1996 | Bierman |
| D377,831 S | 2/1997 | Bierman |
| 5,605,546 A | 2/1997 | Wolzinger et al. |
| 5,664,581 A | 9/1997 | Ashley |
| 5,681,290 A | 10/1997 | Alexander |
| 5,685,859 A | 11/1997 | Kornerup |
| 5,686,096 A | 11/1997 | Khan et al. |
| 5,690,616 A | 11/1997 | Mogg |
| 5,693,032 A | 12/1997 | Bierman |
| 5,702,371 A | 12/1997 | Bierman |
| 5,722,959 A | 3/1998 | Bierman |
| 5,728,053 A | 3/1998 | Calvert |
| 5,800,402 A | 9/1998 | Bierman |
| 5,800,410 A | 9/1998 | Gawreluk |
| 5,810,781 A | 9/1998 | Bierman |
| D399,954 S | 10/1998 | Bierman |
| 5,827,230 A | 10/1998 | Bierman |
| 5,827,239 A | 10/1998 | Dillon et al. |
| 5,833,666 A | 11/1998 | Davis et al. |
| 5,833,667 A | 11/1998 | Bierman |
| 5,855,591 A | 1/1999 | Bierman |
| 5,885,254 A | 3/1999 | Matyas |
| 5,897,519 A | 4/1999 | Shesol et al. |
| 6,050,934 A | 4/2000 | Mikhail et al. |
| D425,619 S | 5/2000 | Bierman |
| 6,099,509 A | 8/2000 | Brown et al. |
| 6,113,577 A | 9/2000 | Hakky et al. |
| 6,132,398 A | 10/2000 | Bierman |
| 6,132,399 A | 10/2000 | Shultz |
| 6,171,594 B1 * | 1/2001 | Nielsen .................. 424/744 |
| 6,213,979 B1 | 4/2001 | Bierman |
| 6,224,571 B1 | 5/2001 | Bierman |
| 6,231,547 B1 | 5/2001 | O'Hara |
| 6,231,548 B1 | 5/2001 | Bassett |
| 6,258,066 B1 | 7/2001 | Urich |
| 6,283,945 B1 | 9/2001 | Bierman |
| 6,290,676 B1 | 9/2001 | Bierman |
| 6,361,523 B1 | 3/2002 | Bierman |
| 6,375,639 B1 | 4/2002 | Duplessie |
| 6,413,240 B1 | 7/2002 | Bierman et al. |
| 6,428,515 B1 | 8/2002 | Bierman et al. |
| 6,428,516 B1 | 8/2002 | Bierman et al. |
| 6,436,073 B1 | 8/2002 | Von Teichert |
| 6,447,485 B2 | 9/2002 | Bierman |
| 6,447,486 B1 | 9/2002 | Tollini |
| 6,471,676 B1 | 10/2002 | DeLegge et al. |
| 6,482,183 B1 | 11/2002 | Pausch |
| 6,491,664 B2 | 12/2002 | Bierman |
| 6,500,154 B1 | 12/2002 | Hakky et al. |
| D469,530 S | 1/2003 | Gomez |
| D470,936 S | 2/2003 | Bierman |
| 6,517,522 B1 | 2/2003 | Bell |
| 6,551,285 B1 | 4/2003 | Bierman |
| 6,572,588 B1 | 6/2003 | Bierman et al. |
| 6,582,403 B1 | 6/2003 | Bierman et al. |
| 6,616,635 B1 | 9/2003 | Bell |
| 6,626,890 B2 | 9/2003 | Nguyen et al. |
| 6,652,487 B1 | 11/2003 | Cook |
| 6,663,600 B2 | 12/2003 | Bierman et al. |
| 6,689,104 B2 | 2/2004 | Bierman |
| D492,411 S | 6/2004 | Bierman |
| 6,770,055 B2 | 8/2004 | Bierman et al. |
| 6,786,892 B2 | 9/2004 | Bierman |
| 6,809,230 B2 | 10/2004 | Hancock et al. |
| 6,827,705 B2 | 12/2004 | Bierman |
| 6,827,706 B2 | 12/2004 | Tollini |
| 6,827,707 B2 | 12/2004 | Wright et al. |
| 6,834,652 B2 | 12/2004 | Altman |
| 6,837,875 B1 | 1/2005 | Bierman |
| 6,866,652 B2 | 3/2005 | Bierman |
| D503,977 S | 4/2005 | Bierman |
| 6,951,550 B2 | 10/2005 | Bierman |
| 6,972,003 B2 | 12/2005 | Bierman |
| 6,979,320 B2 | 12/2005 | Bierman |
| 6,981,969 B2 | 1/2006 | Chavez et al. |
| 7,014,627 B2 | 3/2006 | Bierman |
| 7,018,362 B2 | 3/2006 | Bierman |
| 7,070,580 B2 | 7/2006 | Nielsen |
| 7,090,660 B2 | 8/2006 | Roberts et al. |
| D528,206 S | 9/2006 | Bierman |
| 7,153,291 B2 | 12/2006 | Bierman |
| 7,354,421 B2 | 4/2008 | Bierman |
| 2002/0068904 A1 | 6/2002 | Bierman et al. |
| 2002/0099360 A1 | 7/2002 | Bierman |
| 2002/0133121 A1 | 9/2002 | Bierman |
| 2003/0055382 A1 | 3/2003 | Schaeffer |
| 2003/0229313 A1 | 12/2003 | Bierman |
| 2004/0102736 A1 | 5/2004 | Bierman |
| 2004/0111067 A1 | 6/2004 | Kirchhofer |
| 2004/0204685 A1 | 10/2004 | Wright et al. |
| 2005/0182367 A1 | 8/2005 | Walborn |
| 2005/0215953 A1 | 9/2005 | Rossen |
| 2005/0288635 A1 | 12/2005 | Davis et al. |
| 2006/0015076 A1 | 1/2006 | Heinzerling et al. |
| 2006/0064063 A1 | 3/2006 | Bierman |

(56) References Cited

U.S. PATENT DOCUMENTS

| | | |
|---|---|---|
| 2006/0135944 A1 | 6/2006 | Bierman |
| 2006/0184127 A1 | 8/2006 | Bierman |
| 2006/0184129 A1 | 8/2006 | Bierman |
| 2006/0217669 A1* | 9/2006 | Botha .......................... 604/177 |
| 2006/0247577 A1 | 11/2006 | Wright |
| 2006/0264836 A1 | 11/2006 | Bierman |
| 2006/0270995 A1 | 11/2006 | Bierman |
| 2008/0045905 A1 | 2/2008 | Chawki |

FOREIGN PATENT DOCUMENTS

| | | |
|---|---|---|
| EP | 0356683 | 3/2000 |
| FR | 2 922 458 A1 | 4/2009 |
| WO | WO 94/21319 | 9/1994 |
| WO | WO 97/15337 | 5/1997 |
| WO | WO 99/55409 | 11/1999 |

* cited by examiner

STABILIZATION DEVICE WITH INTEGRATED DRESSING

RELATED APPLICATION

This application is the National Stage of International Application No. PCT/US2010/035011, filed on May 14, 2010, entitled "Stabilization Device with Integrated Dressing," which claims the benefit of U.S. Provisional Application No. 61/178,928, filed May 15, 2009, entitled "Universal Stabilization Device," the disclosure of each of which is hereby incorporated by reference in its entirety.

BACKGROUND OF THE INVENTION

1. Field of the Invention

This application is directed to a stabilization device for stabilizing a medical article, such as a catheter, near an insertion site. More particularly, this application is directed to a stabilization device having an integrated dressing.

2. Description of the Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical article properly positioned for the duration of treatment, the catheter or medical article can be secured to the patient in a variety of ways. Most commonly, this involves taping or suturing the catheter or medical article to the patient.

Securing a catheter with tape upon the patient traditionally has certain drawbacks. The use of tape at the insertion site can retain dirt or other contaminant particles, potentially leading to infection of the patient. Tape also fails to limit catheter motion and, therefore, contributes to motion related complications like phlebitis, infiltration and catheter migration. Additionally, removal of taped dressings can itself cause undesired motion of the catheter upon the patient.

Taped dressings also require periodic changes. The frequent, often daily, removal and reapplication of adhesive tape to the skin of the patient can excoriate the skin. Such repeated applications of tape over the catheter or medical article can additionally lead to the build up of adhesive residue on the outer surface of the catheter or medical article. This residue can result in contaminants adhering to the medical article itself, increasing the likelihood of infection of the insertion site. This residue can also make the catheter or medical article stickier and more difficult to handle for healthcare providers.

Suturing also carries risk, both to healthcare workers and patients. Healthcare workers can suffer accidental needlestick injury, which may expose them to hepatitis, HIV, and other pathogens. Patients can suffer local or even systemic infection from suture, as well as scarring and pain.

SUMMARY OF THE INVENTION

One aspect of the present invention is a securement system comprising a medical article comprising a connector fitting and a catheter hub, first and second anchor pads, each anchor pad being spaced apart from the other, a retainer comprising a body member having a channel formed therethrough about a channel axis, the channel being configured to retain at least a first portion of the medical article and having a first longitudinal access opening disposed on an underside of the body member to allow at least ingress of the first portion of the medical article into the channel, two support members, each support member being attached to one of the anchor pads and configured to support the body member, each support member being spaced apart from the channel axis so as not to obstruct at least ingress of the first portion of the medical article into the channel, and a first abutment surface extending generally normal to the channel axis and configured to inhibit longitudinal movement of the medical article in a first longitudinal direction, and a dressing member connected to the first and second anchor pads, the dressing member having a first region extending proximally of the first anchor pad, a second region extending proximally of the second anchor pad, and a third region connecting the first and second regions, the dressing member having a lower surface at least partially covered by an adhesive for contacting the patient's skin, the dressing member further defining an open region proximal of the longitudinal access opening of the body member, the open region being configured to allow clearance of the dressing member over the medical article during application of the dressing member to the patient's skin.

Another aspect is a device for securing a medical article to a patient and covering an insertion site, the device comprising a retainer having a channel for receiving at least a portion of a medical, at least one anchor pad supporting the retainer, and a dressing member connected to the at least anchor pad, the dressing member being sized so as to cover an insertion site.

Another aspect is a method of securing a medical article to a patient near an insertion site, the method comprising providing a securement device comprising first and second anchor pads being spaced apart from one another, a retainer having a channel formed therethrough, the channel being configured to receive at least a portion of the medical article and having a first longitudinal access opening disposed on an underside of the retainer, first and second supports supporting the retainer, and a dressing member connected to the first and second anchor pads, the dressing member having a first region extending proximally of the first anchor pad, a second region extending proximally of the second anchor pad, and a third region connecting the first and second regions, the dressing member further defining an open region proximal of the longitudinal access opening of the retainer, the open region being configured to allow clearance of the dressing member over the medical article during application of the dressing member to the patient's skin, locating the securement device above the medical article so as to align the portion of the medical article with the channel of the securement device, pressing the portions of the medical article through the access opening and into the channel so as to limit movement of the medical article in at least lateral and transverse directions relative to the securement device, adhering the first and second anchor pads to the patient's skin distal of the insertion site, and adhering the dressing member to the patient's skin so as to cover the insertion site.

BRIEF DESCRIPTION OF THE DRAWINGS

The above-mentioned and other features of the invention will now be described with reference to the drawings of various embodiments which are intended to illustrate but not to limit the invention. The drawings contain the following figures.

DETAILED DESCRIPTION OF THE PREFERRED EMBODIMENT

The following description and the accompanying figures, which describe and show the preferred embodiments, are made to demonstrate several possible configurations that a stabilization system can take to include various aspects and features the invention. The illustrated embodiments are shown in use with an illustrative example of a catheter hub, an illustrative example of an extension set for connection to the stabilization system, and/or an illustrative example of a connector fitting with a spin nut for connection to the catheter hub. The illustration of the stabilization device in this context is not intended to limit the disclosed aspects and features of the invention to the specified embodiments or to usage only with the illustrated hub, extension set, or connector. Those of skill in the art will recognize that the disclosed aspects and features of the invention are not limited to any particular embodiment of a stabilization system, and stabilization systems, which include one or more of the inventive aspects and features herein described, can be designed for use with a variety of medical articles.

Figure 1:
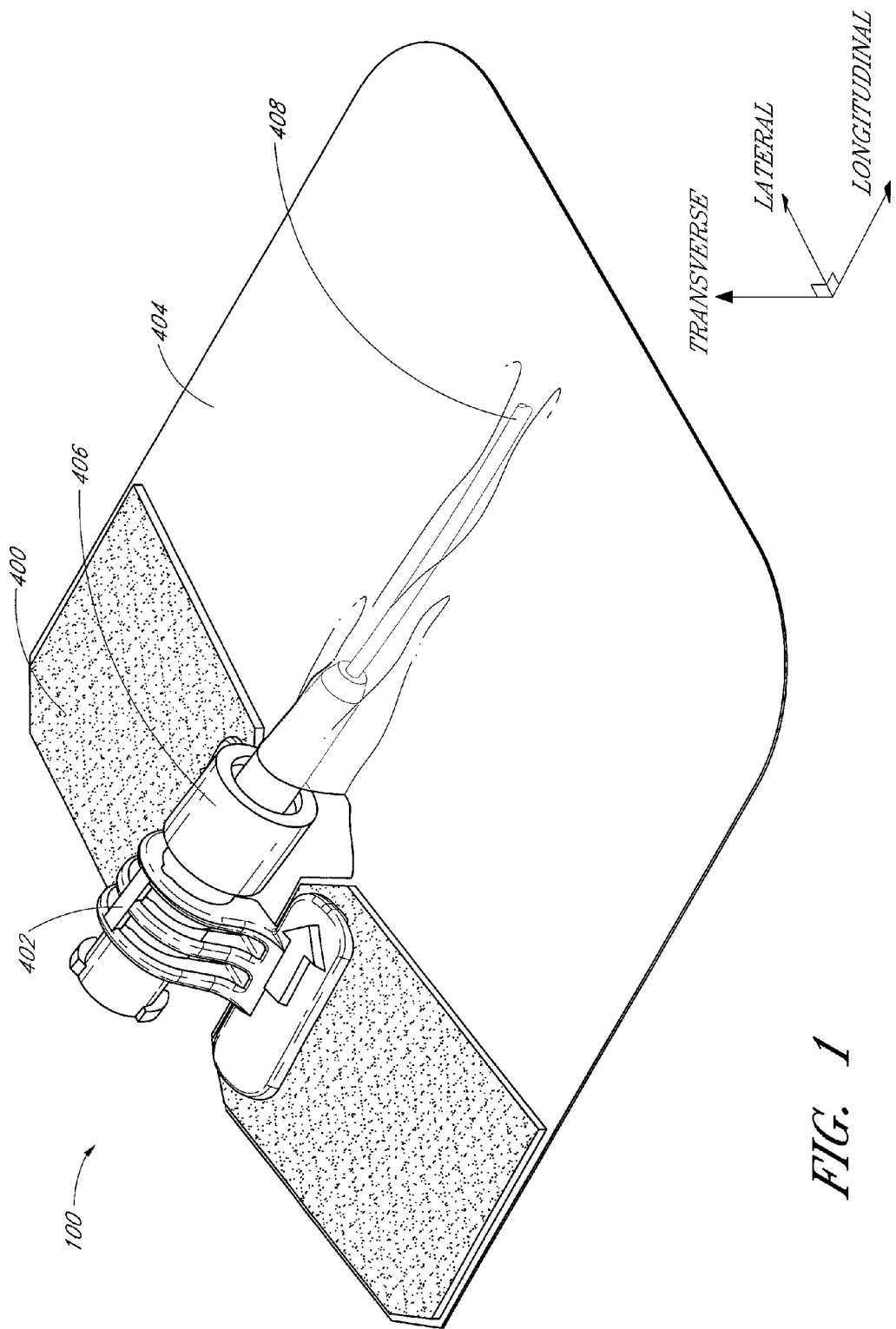
FIG. 1 is an isometric view of a stabilization device having an integrated anchor pad and dressing, configured in accordance with a preferred embodiment of the present invention and shown securing an exemplary medical article.

To assist in the description of these components of the stabilization system, the following coordinate terms are used (see FIG. 1). A "longitudinal axis" is generally parallel to a portion of the catheter hub or other medical article connected to the stabilization system, as well as parallel to the axis of a channel of the stabilization device. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the channel or connector fitting, and therefore is substantially synonymous with the term "longitudinal" as used herein. Also, the terms "proximal" and "distal", which are used to describe the present stabilization system, are used consistently with the description of the exemplary applications (i.e., the illustrative examples of the use applications). Thus, proximal and distal are used in reference to the center of the patient's body. The terms "upper," "lower," "top," "bottom," "underside," "upperside" and the like, which also are used to describe the present stabilization system, are used in reference to the illustrated orientation of the embodiment. For example, the term "upperside" is used to describe the portion of the stabilization device that is located above a lateral axis that passes through the axis of the channel. The term "underside" is used to describe the portion of the stabilization device that is located below a lateral axis that passes through the axis of the channel. Brief introductions to some of the features, which are common to the described embodiments of the stabilization systems, are now described. In the illustrated embodiment, the arrows on the stabilization device point in the direction toward the insertion site (i.e., in the proximal direction).

The preferred embodiments of the present invention advantageously provide a stabilization system for stabilizing a medical article, such as a catheter, to the skin of a patient near an insertion site. Embodiments generally include an anchor pad, a stabilization device (for example, a retainer configured to secure a connector fitting or other medical article, or a catheter stabilization device comprising an integral adapter) disposed on the anchor pad, and a dressing feature connected to the anchor pad. Such a combined anchor pad and dressing feature can be included independent of the structure of the stabilization device (or retainer) itself In some embodiments, the stabilization device comprises a medical line securement system for securing a medical article to a patient. The medical article can have an elongated body. The elongated body cooperates with a retainer forming part of the stabilization device, to arrest movement of the medical article in longitudinal, lateral, and transverse directions when placed within the retainer.

Figure 2:
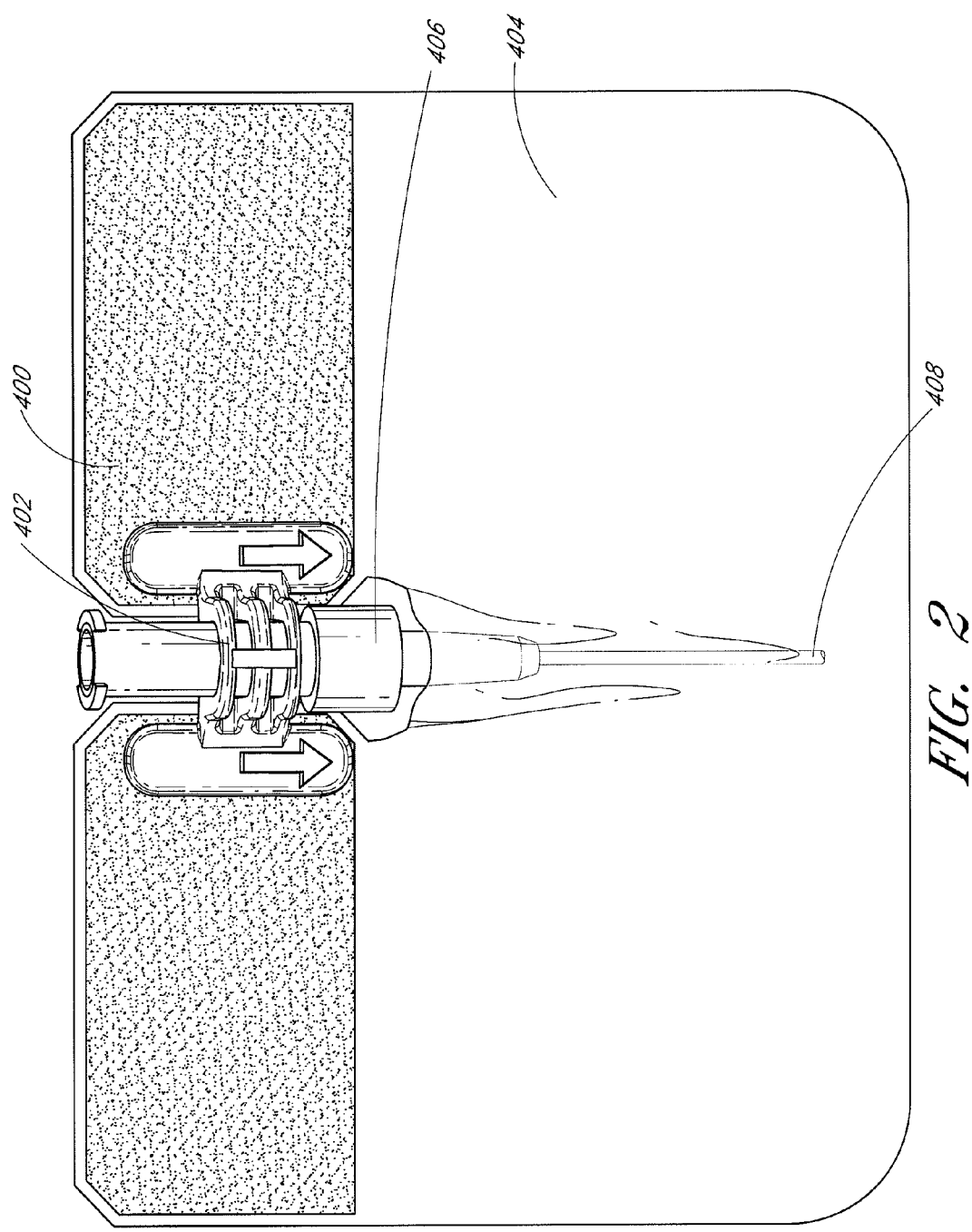
FIG. 2 is a top plan view of the stabilization device of FIG. 1.
Figure 3:
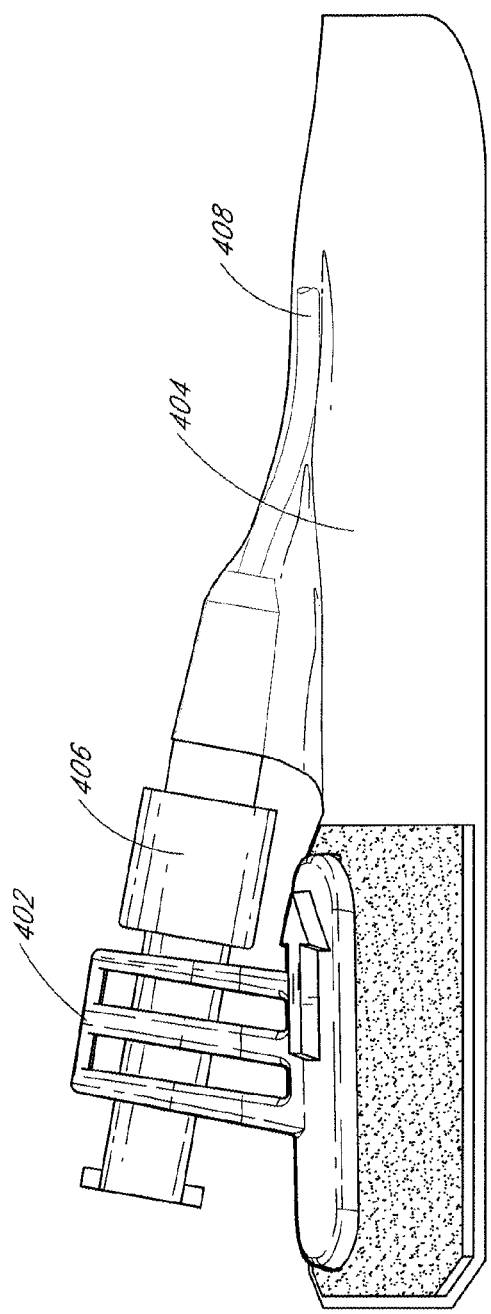
FIG. 3 is a side view of the stabilization device of FIG. 1.

With reference to FIGS. 1 through 3, a stabilization system 100 in accordance with an embodiment is illustrated. The stabilization system 100 includes a retainer 402 which is configured to secure a medical article relative to a patient. Exemplary medical articles include connector fittings and catheter hubs. The medical article may include a spin nut or other structure for engaging with a catheter. The medical article can include a combined retainer/medical article or other stabilization device. The retainer 402 is shown securing an exemplary medical article 406.

The stabilization system 100 comprises an anchor pad 400 and an integral dressing 404. The dressing 404 in the illustrated embodiment extends in a proximal direction from the anchor pad 400. Either or both of the anchor pad 400 and the dressing 404 can comprise a laminate structure, as described in further detail below. The dressing 404 can extend from the anchor pad 400 by an amount sufficient to allow the dressing to completely cover the insertion site 408. In preferred embodiments, at least a portion of the dressing 404 is transparent to provide for visibility of the insertion site. By such a configuration, only one step is required of the practitioner to secure the system 100 to the patient's skin, and to cover and thus protect the insertion site 408.

Figure 4:
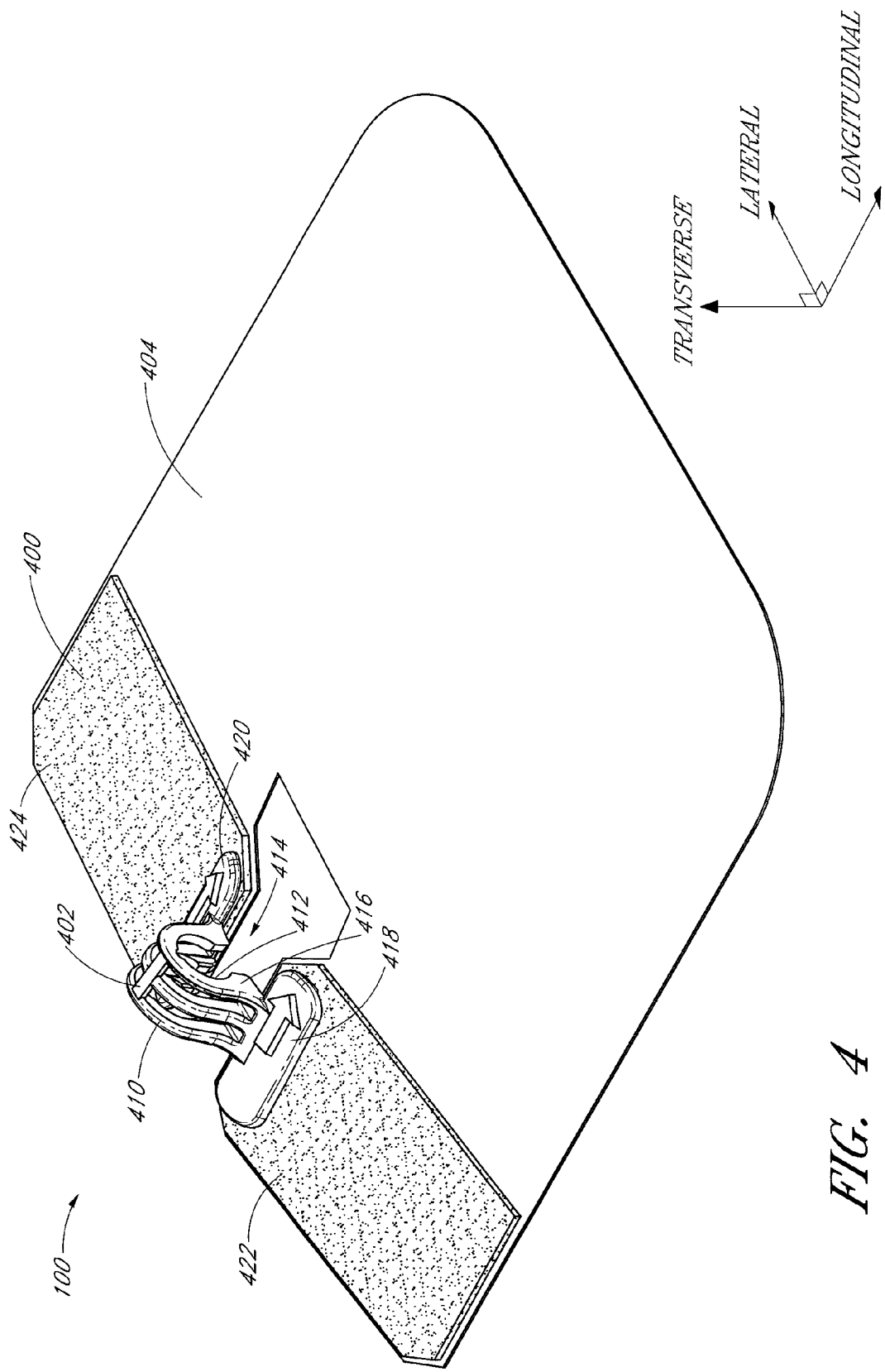
FIG. 4 is an isometric view of the stabilization device of FIG. 1, shown without the medical article.
Figure 5:
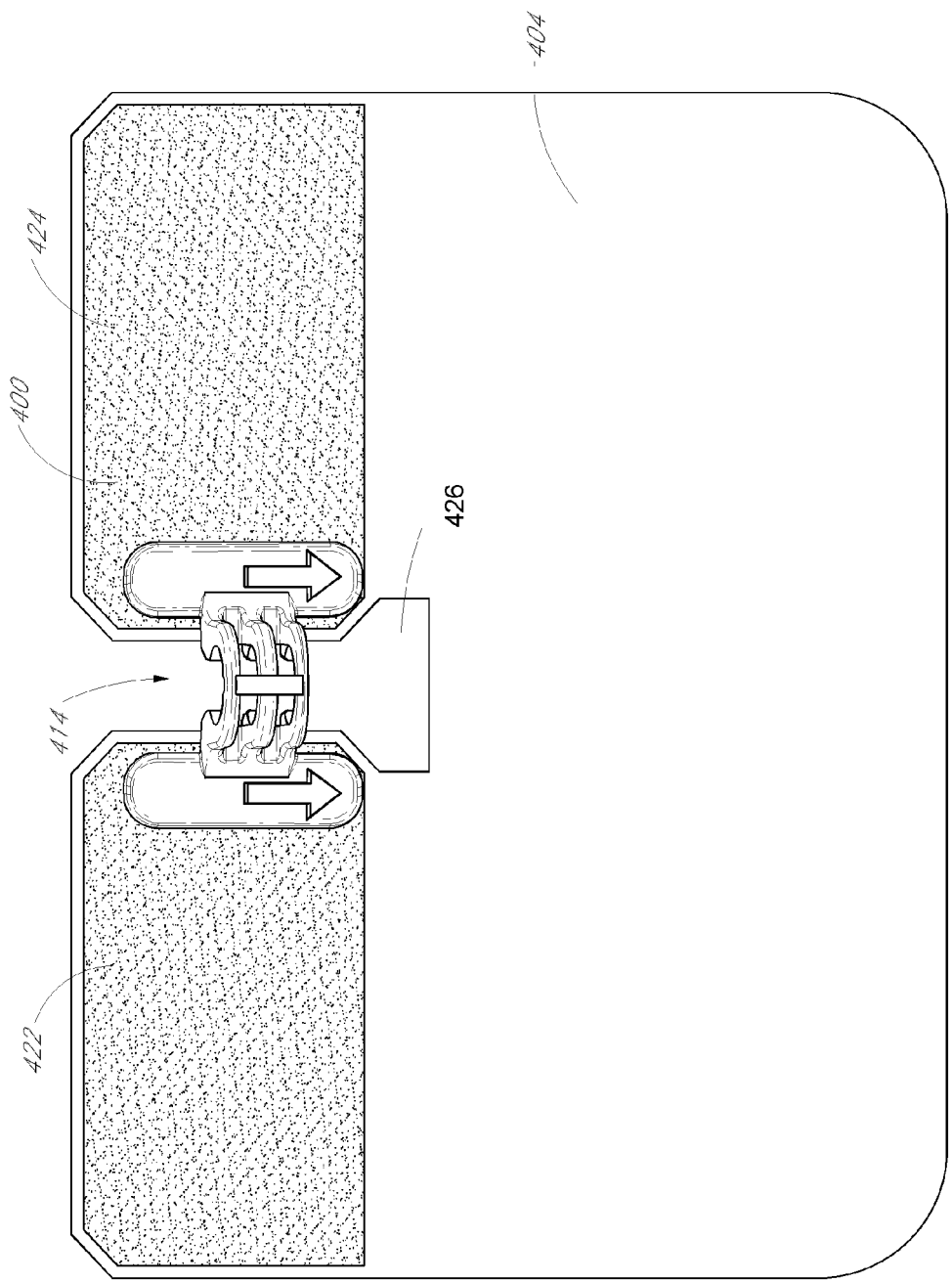
FIG. 5 is a top plan view of the stabilization device of FIG. 1, shown without the medical article.
Figure 6:
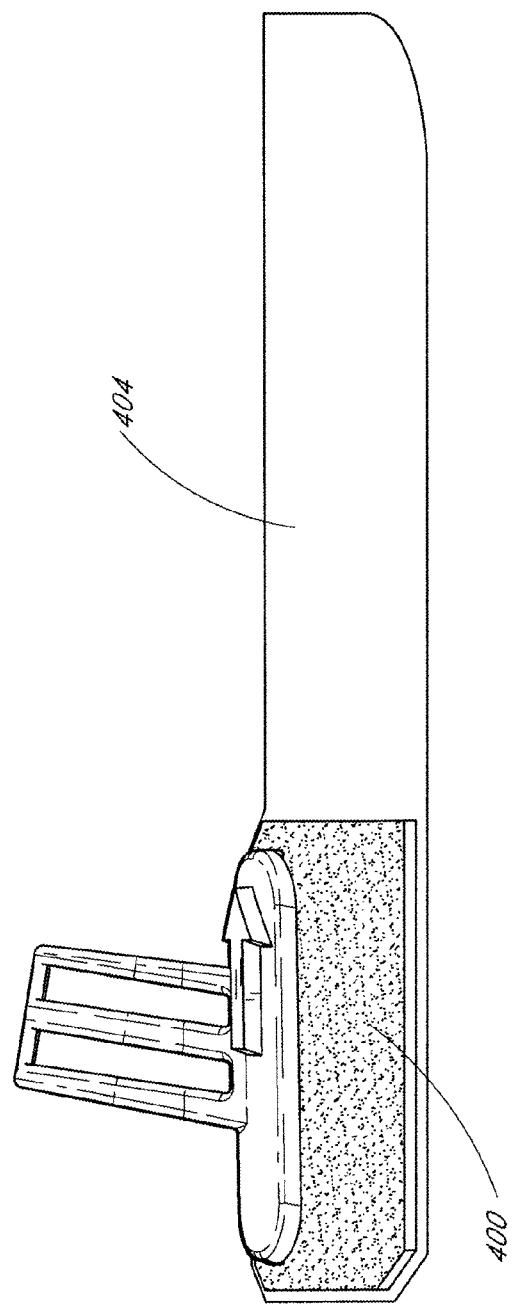
FIG. 6 is a side view of the stabilization device of FIG. 1, shown without the medical article.

FIGS. 4 through 6 illustrate the stabilization system 100 without the medical article 406. As shown in these figures, the retainer 402 has a body member 410 which includes an inverted channel 412 formed therethrough. The inverted channel 412 has a longitudinal access opening 414 located on an underside of the retainer 402 to allow ingress or egress of the medical article. The medical article is installed or removed from the underside of the retainer 402 via this access opening 414. Such an arrangement allows the medical provider to align at least a portion of the medical article with the retainer 402 prior to fixing the retainer to the patient's skin. In this way, the inverted channel 412 retains a portion of the medical article.

In some embodiments, the retainer 402 includes at least one abutment (preferably an abutment surface) that cooperates with at least one contact point or surface on the medical article. The one or more abutments of the retainer extend generally normal to the axis of the channel and can be, for example, but without limitation a surface, a wall of a slot, a ridge, a protuberance, or like structures. The abutment cooperates with the one or more contact points or surfaces of the medical article to inhibit longitudinal movement of the medical article through the channel. For example, the abutment could be a surface on the distal end of the retainer that acts against at least a portion of a radially extending member or spin nut of the medical article. In this way, the medical article will be limited in it proximal movement (i.e., movement toward the patient) once the radially extending member contacts or abuts against the distal end of the retainer.

In some embodiments, the retainer further includes at least one support 416 that is preferably disposed on the underside of the retainer 402 at a position lower than the access opening 414. With this construction, the retainer 402 holds the retained portion of medical article away from the patient's skin, when the retained portion is positioned within the retainer channel 412, to avoid chafing or excoriating the skin. The support 416 can include left and right mounting wings 418, 420 that are integral with the body member and are attached to left and right anchor pads 422, 424. The lower surfaces of the left and right anchor pads 422, 424 attach to the patient's skin.

The retainer 402 and anchor pad(s) 422, 424 also can have other constructions in order to inhibit contact between the skin and the retainer, as well as between the skin and the retained portion of the medical article. For example, the anchor pads can be thicker, in which case the mounting wings can be located higher on the retainer body.

As illustrated in FIG. 5, the dressing 404 is configured with an essentially U-shaped configuration. That is, the dressing 404 extends proximally from the anchor pads 422, 424 on either side of the access opening 414. An open region 426 is provided in the dressing material proximal of the access opening 414, which open region allows the dressing portion 404 to clear the medical article during the process of attaching the system 100 to a patient's skin.

In some embodiments, the stabilization device can form a component of a catheterization or securement system that also includes one or more medical articles, such as connector fittings, catheters, hubs, catheter adaptors, fluid supply lines, or other articles suitable for securement via the anchor pads and retainer.

In addition to incorporating the stabilization portion and dressing into one integrated system, the dressing can also be made of hydrocolloid—a material that can be impregnated with various other compounds that improve the application of the device and the overall comfort of the patient. Some hydrocolloid compounds include but are not limited to: skin prep, aloe vera, vitamin C, vitamin E, antimicrobial agent, etc. In some embodiments, a transparent peel liner can be employed to provide visibility to the practitioner while applying the retainer or other stabilization device. The two-in-one system reduces the number of components and steps required during the application of the catheter and its stabilization. This new combined system reduces clinician time and the number of components required in the process.

In some embodiments, the anchor pad or pads can comprise a generally rectangular shape. In some embodiments, the anchor pads can have a scalloped region located at a corner of each anchor pad, to ease the process of aligning the stabilization device with a catheter insertion site in the patient's skin. Those of skill in the art will recognize that a variety of anchor pad shapes can also be used.

Each anchor pad desirably comprises a laminate structure with an upper plastic, paper or foam layer (e.g., closed-cell polyethylene foam) and a lower adhesive layer. The lower adhesive layer constitutes a lower surface of the anchor pad. The lower surface desirably is a medical-grade adhesive and can be either diaphoretic or nondiaphoretic, depending upon the particular application. Such foam with an adhesive layer is available commercially from Avery Dennison of Painsville, Ohio. While not illustrated, the anchor pads can include suture holes in addition to the adhesive layer to further secure the anchor pad to the patient's skin.

In other variations, a hydrocolloid adhesive or zinc oxide-based adhesive can advantageously be used upon the anchor pads for attaching the anchor pads to the skin of the patient. The hydrocolloid or zinc oxide-based adhesive can be used either alone or in combination with another medical grade adhesive (e.g., in combination with the adhesive available from Avery Dennison). Hydrocolloid and zinc oxide-based adhesives have less of a tendency to excoriate the skin of a patient when removed. This can be particularly important for patients whose skin is more sensitive or fragile, such as neonates and those with a collagen deficiency or other skin related condition.

In another variation, each anchor pad comprises a laminate structure with an upper woven layer and a lower adhesive layer. The upper layer can be polyester or other suitable polymer or textile materials. One particular suitable material is a woven polyester available commercially under the name "Tricot" from Tyco. The lower adhesive layer constitutes the lower surface of the anchor pad. The lower surface desirably is a medical-grade adhesive and can be either diaphoretic or nondiaphoretic, depending upon the particular application.

A surface of the upper foam layer constitutes an upper surface of the anchor pads. The upper surface can be roughened by corona-treating the foam with a low electric charge. The roughened or porous upper surface can improve the quality of the adhesive joint (which is described below) between the mounting wings and the anchor pads. In a further variation, the flexible anchor pad can comprise an upper paper or other woven or nonwoven cloth or plastic layer in lieu of a roughened upper foam surface.

In some embodiments, the anchor pads 422, 424 preferably are arranged with respect to the stabilization device such that the proximal tip of the adapter does not extend beyond the front edge of the mounting wings 418, 420.

A removable paper or plastic release liner desirably covers the adhesive lower surface before use. The liner preferably resists tearing and desirably is divided into a plurality of pieces to ease attachment of the pad to a patient's skin. The liner comprises a folded over portion to define a pull tab. The pull tab can be utilized to remove the paper or plastic release liner from their adhesive lower surface before use. A healthcare provider uses the pull tab by grasping and pulling on it so that the liner is separated from the lower surface. The pull tab overcomes any requirement that the healthcare provider pick at a corner edge or other segment of the liner in order to separate the liner from the adhesive layer.

The pull tab of course can be designed in a variety of configurations. For example, the pull tab can be located along a center line of the anchor pad 422, 424; or alternatively, the pull tab can be located along any line of the anchor pad in order to ease the application of the anchor pad onto the patient's skin at a specific site. For example, an area of a patient's skin with an abrupt bend, such as at a joint, can require that the pull tab be aligned toward one of the lateral ends of the anchor pad rather than along the center line. In some embodiments, the pull tab extends from a bottom surface of the anchor pads and along an outer line.

The fold that forms the pull tab preferably occurs laterally beyond the inner (medial) edge on each anchor pad rather than at the inner edge of the anchor pad 422, 424. Thus, the spacing between the folds of the release liners is less than the spacing between the inner edges of the anchor pads. The projection of the release linear beyond the anchor pad inner edge provides an area onto which any adhesive, which is used to attach the stabilization device to the anchor pad, can run while lessening the occurrence of such adhesive contacting the fold. Cracks often occur at the fold and presence of adhesive in such cracks can create delimitation of the release liner and incomplete removal of the release linear when peeled away from the corresponding anchor pad.

Additionally, the distal side of each release linear can be cut to increase a "view window" through which a healthcare provider can see when aligning the stabilization device near the insertion site. Preferably, the resulting relief originates from the inner edge of the release linear generally at a right angle thereto and then transitions into a shape that generally matches the shape of the adjacent region of corresponding anchor pad 422, 424. The initial right-angle cut of this relief reduces instances of the release linear ripping when properly pulled in the lateral direction away from the stabilization device.

It is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Although these techniques and systems have been disclosed in the context of certain embodiments and examples, it will be understood by those skilled in the art that these techniques and systems may be extended beyond the specifically disclosed embodiments to other embodiments and/or uses and obvious modifications and equivalents thereof Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the systems disclosed herein disclosed should not be limited by the particular disclosed embodiments described above but by a fair reading of the claims which follow.

What is claimed is:

1. A securement system comprising:
    a medical article comprising a connector fitting and a catheter hub;
    first and second anchor pads, each anchor pad being spaced apart from the other;
    a retainer comprising,
        a body member having a channel formed therethrough about a channel axis, the channel being configured to retain at least a first portion of the medical article and having a longitudinal access opening disposed on an underside of the body member to allow at least ingress of the first portion of the medical article into the channel,
        two support members, each support member being attached to one of the anchor pads and configured to support the body member, each support member being spaced apart from the channel axis so as not to obstruct at least ingress of the first portion of the medical article into the channel, and
        a first abutment surface extending generally normal to the channel axis and configured to inhibit longitudinal movement of the medical article in a first longitudinal direction; and
    a dressing member connected to the first and second anchor pads, the dressing member having a first region extending proximally of the first anchor pad, a second region extending proximally of the second anchor pad, and a third region connecting the first and second regions, the dressing member having a lower surface at least partially covered by an adhesive for contacting the patient's skin, the dressing member further defining an open region proximal of the longitudinal access opening of the body member, the open region extending in a distal direction between the first and second anchor pads so as to allow at least ingress of the first portion of the medical article into the channel from a location below the first and second anchor pads when the dressing member is connected to the first and second anchor pads, the open region being configured to allow clearance of the dressing member over the medical article during application of the dressing member to the patient's skin.

2. The system of claim 1, wherein the dressing member extends at least partially underneath the first and second anchor pads.

3. The system of claim 1, wherein the dressing member extends at least partially over the first and second anchor pads.

4. The system of claim 1 further comprising a removable liner covering the lower surface of the dressing member.

5. The system of claim 1, wherein the dressing member comprises a hydrocolloid material.

6. The system of claim 5, wherein the hydrocolloid material comprises aloe vera.

7. The system of claim 5, wherein the hydrocolloid material comprises an antimicrobial agent.

8. A device for securing a medical article to a patient and covering an insertion site, the device comprising:
    a retainer having a channel for receiving at least a portion of a medical article;
    at least one anchor pad supporting the retainer so that the channel is disposed above the at least one anchor pad; and
    a dressing member connected to the at least anchor pad, the dressing member being sized so as to cover an insertion site and having an open region, the open region extending in a distal direction below the channel so as to allow at least ingress of the medical article into the channel from a location below the at least one anchor pad when the dressing member is connected to the at least one anchor pad.

9. The device of claim 8, wherein the dressing member is generally U-shape.

10. The device of claim 8, wherein the retainer directly secures to both the at least one anchor pad and the dressing member.

11. The device of claim 8, wherein the retainer directly secures to the at least one anchor pad.

12. The device of claim 8, wherein the dressing member has a thickness that is less than a thickness of the at least one anchor pad.

13. The device of claim 8, wherein the dressing member is transparent and the anchor pad is opaque.

14. The device of claim 8, wherein the dressing member extends at least partially underneath the at least one anchor pad.

15. The device of claim 8, wherein the dressing member extends at least partially over the at least one anchor pad.

16. The device of claim 8 further comprising a removable liner covering a lower surface of the dressing member.

17. The device of claim 8, wherein the dressing member comprises a hydrocolloid material.

18. The device of claim 17, wherein the hydrocolloid material comprises aloe vera.

19. The device of claim 17, wherein the hydrocolloid material comprises an antimicrobial agent.

20. A method of securing a medical article to a patient near an insertion site, the method comprising:

providing a securement device comprising first and second anchor pads being spaced apart from one another, a retainer having a channel formed therethrough, the channel being configured to receive at least a portion of the medical article and having a longitudinal access opening disposed on an underside of the retainer, first and second supports supporting the retainer, and a dressing member connected to the first and second anchor pads, the dressing member having a first region extending proximally of the first anchor pad, a second region extending proximally of the second anchor pad, and a third region connecting the first and second regions, the dressing member further defining an open region proximal of the longitudinal access opening of the retainer, the open region being configured to allow clearance of the dressing member over the medical article during application of the dressing member to the patient's skin;

locating the securement device above the medical article so as to align the portion of the medical article with the channel of the securement device;

pressing the portions of the medical article through the access opening and into the channel from a location below the first and second anchor pads when the dressing member is connected to the first and second anchor pads so as to limit movement of the medical article in at least lateral and transverse directions relative to the securement device;

adhering the first and second anchor pads to the patient's skin distal of the insertion site; and adhering the dressing member to the patient's skin so as to cover the insertion site.

* * * * *